(12) United States Patent
Alvarado et al.

(10) Patent No.: US 10,123,812 B1
(45) Date of Patent: Nov. 13, 2018

(54) 3-D FEMUR ORTHOPEDIC DRILL GUIDE

(71) Applicants: Carlos A. Alvarado, San Juan, PR (US); Gilberto J. Alvarado, Ponce, PR (US)

(72) Inventors: Carlos A. Alvarado, San Juan, PR (US); Gilberto J. Alvarado, Ponce, PR (US)

( * ) Notice: Subject to any disclaimer, the term of this patent is extended or adjusted under 35 U.S.C. 154(b) by 0 days.

(21) Appl. No.: 15/853,802

(22) Filed: Dec. 24, 2017

Related U.S. Application Data

(62) Division of application No. 15/442,353, filed on Feb. 24, 2017, now Pat. No. 9,848,895.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/17* | (2006.01) | |
| *A61B 17/16* | (2006.01) | |
| *A61B 17/00* | (2006.01) | |

(52) U.S. Cl.
CPC ...... *A61B 17/1714* (2013.01); *A61B 17/1675* (2013.01); *A61B 17/1764* (2013.01); *A61B 2017/00367* (2013.01); *A61B 2017/00477* (2013.01)

(58) Field of Classification Search
CPC combination set(s) only.
See application file for complete search history.

(56) References Cited

U.S. PATENT DOCUMENTS

2011/0313478 A1\* 12/2011 Herdrich ............ A61B 17/1764
606/86 R

\* cited by examiner

*Primary Examiner* — Sameh Boles
(74) *Attorney, Agent, or Firm* — Luis Figarella

(57) ABSTRACT

A three-dimensional (3-D) orthopedic drill guide device for accommodating a bone drill during an orthopedic surgery is disclosed. By establishing two specific angles in relation to the bone fascia, the device acts as a guide for bone drilling locations. In one specific instance, it is an optimal 3-D drill guide for the direction and Gamma angle (resulting from the devices Alpha and Beta angles of the device) of a drill hole in a femoral bone when used to replace an injured anterior cruciate ligament (ACL).

6 Claims, 14 Drawing Sheets

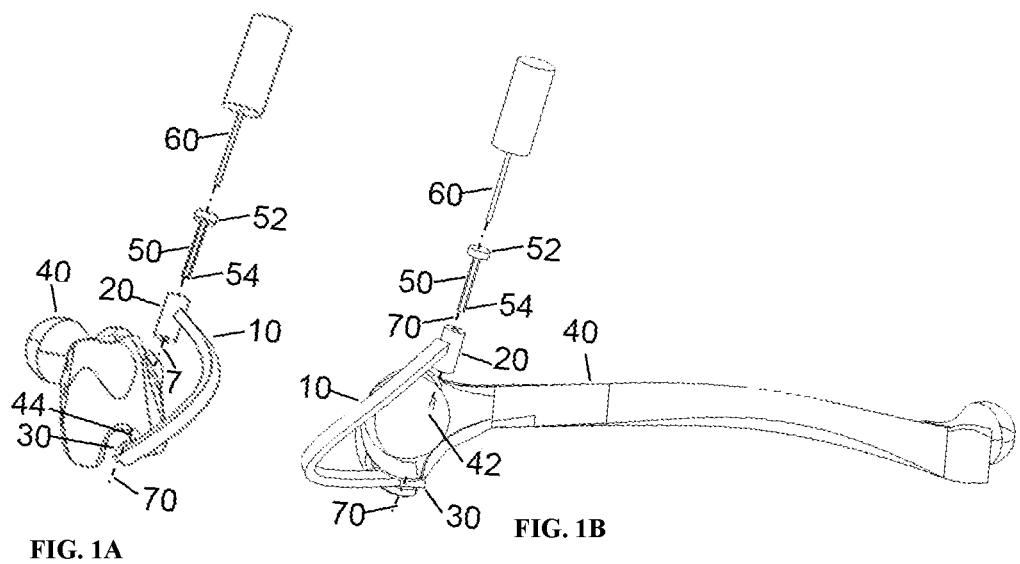
FIG. 1A
FIG. 1B
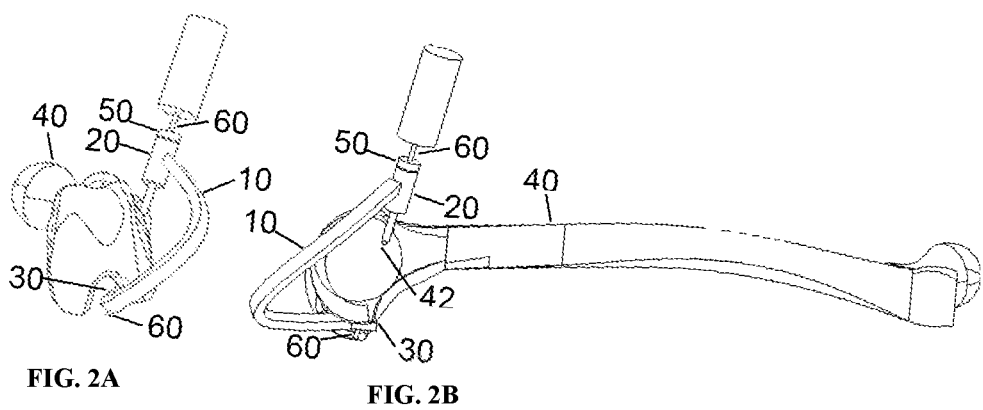
FIG. 2A
FIG. 2B

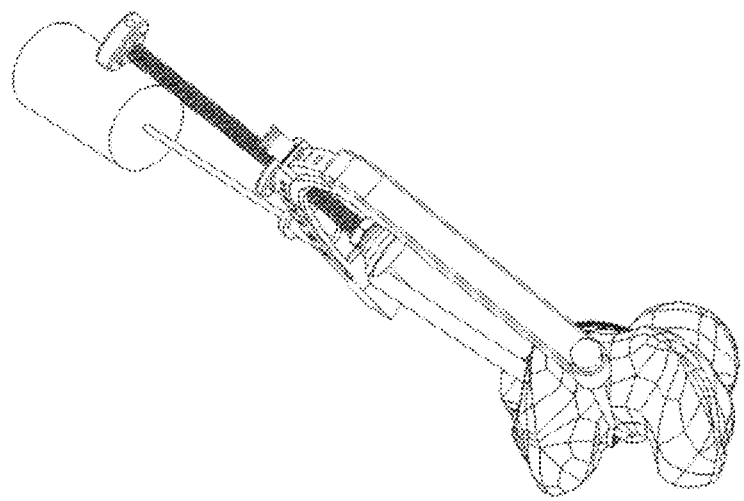
Figure 22
Figure 23
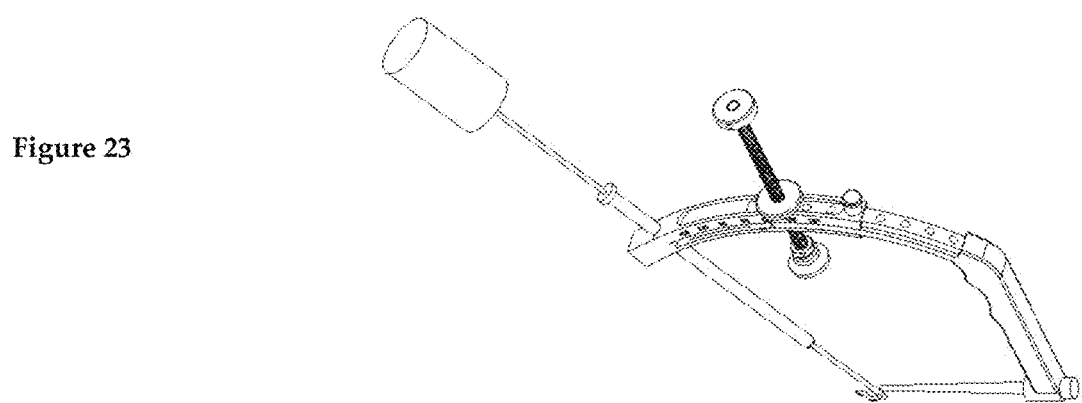

US 10,123,812 B1

3-D FEMUR ORTHOPEDIC DRILL GUIDE

CROSS-REFERENCE TO RELATED APPLICATIONS

This application is a Divisional Continuation application of co-pending U.S. patent application Ser. No. 14/442,353 titled "3-D FEMUR ORTHOPEDIC DRILL GUIDE", filed on Feb. 24, 2017 the disclosure of which is herein incorporated by reference in its entirety.

PATENTS CITED

The following documents and references are incorporated by reference in their entirety, Herdrich (US Pat. Pub. No. 2011/0313478), Whelan (U.S. Pat. Nos. 6,132,433, 6,371,124, 6,537,319, 6,733,529 and 6,974,477) and St. Pierre et al (U.S. Pat. No. 7,063,717).

FIELD OF THE INVENTION

This application relates to an orthopedic drill guide device for accommodating a bone drill, and specifically to a 3-D guide for use in orthopedic surgeries.

DESCRIPTION OF THE RELATED ART

Surgery is necessary to replace injured ACL with a tissue repair device. The tissue repair device material can be synthetic or biological. The tissue repair device is implanted through pre-drilled holes in the tibia and femur bones. The tissue repair device is then pulled and secured to bones with screws, staples, sutures, or a combination thereof.

The through hole in the proximal end of the tibia is typically drilled in an outside-in configuration. In the outside-in configuration, the drill enters the anteromedial side of the tibia and exits at the ACL's anatomic attachment site on the tibial plateau.

The through hole in the distal end of the femur can be drilled in either an outside-in or inside-out configuration. The typical outside-in configuration consists of a through hole drilled from the lateral femoral epicondylar area and emerging at the origin of the ACL on the posteromedial aspect of the lateral femoral condyle. To perform the outside-in drilling the patient knee is positioned in flexion. The inside-out configuration is performed in the opposite direction of the outside-in configuration. To perform the inside-out drilling the patient knee is positioned in hyper flexion. Many complications arise when drilling the distal femur tunnel using present orthopedic drill guides.

When drilling the femur following an outside-in configuration, the drill exit needs to avoid contact with adjacent soft tissue. If the drill is not properly oriented it may damage soft tissue including the femoral condyle cartilage, lateral/collateral ligaments, and/or popliteus tendon. Drill guides used for the outside-in configuration are c-clamps and outside guides. These guides are characterized to be planar or two dimensional. Planar guides do not provide the correct three-dimensional (3-D) directional direction required to prevent soft tissue damage. To obtain the appropriate direction the surgeon has to maneuver the drill guide. This process does not guaranty that soft tissue will not be damaged. In order to avoid soft tissue damage the tunnel should exit at the lateral femoral condyle flare.

Planar guides also present the problem that the drilled tunnel length is not precisely controlled. A short tunnel of less than 20 mm reduces contact surface between the tissue repair device and the bone. The reduced contact surface negatively impacts the tissue repair device biological integration and increases its stress concentration. These problems may cause rupture of the tissue repair device. Current guides cannot predict tunnel length accurately which may result in short tunnel length.

The other type of femoral guide is an inside-out instrument. To use these instruments the surgeon needs to reposition the patient from knee flexion to hyper flexion to position orthopedic guide and drill the femur. Additional positioning steps compromises surgeon's vision which may result in medial femoral condyle injury. Another problem of the inside-out configuration is that the resultant tunnel is short in length. Short length tunnel may rupture the tissue repair device.

The resultant orientation of the tissue repair device must avoid its rupture. The tissue repair device direction should imitate the anatomical orientation of the ACL to improve its function.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In accordance with one embodiment a three-dimensional outside-in femoral orthopedic drill guide device for anterior cruciate ligament reconstruction is disclosed. The guide forms a directional vector for the drill that avoids damage to soft tissue, provides proper tunnel length to promote biological integration of the tissue repair device, avoids leg repositioning to drill the tunnel which allows the surgeon to complete the surgery in one position: knee flexion, provides an anatomical similitude to the biological direction of the anterior cruciate ligament reducing its overstress, and eliminates the need to reposition the orthopedic drill guide device to obtain a proper tunnel directional vector. In addition, the orthopedic drill guide device avoids contact between the orthopedic drill guide device with the patella bone and/or the thigh.

In one aspect the invention is about a three-dimensional orthopedic drill guide device comprising a handle having a first end and a second end, an extendable mechanical component having a first end and a second end, said extendable component first end connected to said handle first end, with an opening at or near said extendable component second end, said opening housing a pilot drill guide mechanically secured to said extendable component's second end, said extendable mechanical component having a lock component securing it to said handle's first end; and a device arm mechanically coupled to said handle second end at said arm near end, wherein said arm has a rotationally adjustable end feature located at said atm distal end. In another aspect, said device arm end feature covers an area which is wider than that of said device arm, with said device arm end feature having an opening to allow a drill bit to pass through. In yet another aspect said device arm end feature has a tip protrusion. In another aspect, said handle has an adjustable screw located near said handle's first end, said screw having a leveling pad at a first end.

In yet another aspect, said extendable mechanical component is a slider and said slider lock component is a releasable plunger, said slider distal end opening houses a hollow bullet-shaped pilot, and said pilot is secured to said slider with an adjustable screw located near said slider's distal end, said device arm end feature shape is selected from the group consisting of geometric shapes, said device arm mechanical coupling to said handle is a thumb screw; and said alpha angle may be set from 100 to 130 degrees and said beta angle may be set from five to 175 degrees. In another aspect said extendable mechanical component is comprised of a plug chain of one or more mechanical plugs and said lock component is comprised of a mechanical component, the final plug forming said plug chain distal end houses a hollow bullet-shaped pilot, and said pilot is secured to said plug chain distal end with an adjustable screw, said device arm end feature shape is selected from the group consisting of geometric shapes, said device arm mechanical coupling to said handle is a thumb screw, said alpha angle may be set from 100 to 130 degrees and said beta angle may be set from five to 175 degrees.

In one aspect, the invention is about a three-dimensional orthopedic drill guide device comprising a handle having a first end and a second end, wherein said handle first end has one or more openings capable of housing a pilot drill guide mechanically secured to said handle at an alpha angle wherein said handle second end has an end feature located at said second end distal end, said distal end feature distal end being angled at a beta angle of 5 to 175 degrees. In another aspect, said handle second end feature has an area which is wider than that of said handle, and said end feature has an opening to allow the drill bit to pass through. In yet another aspect said handle second end feature has a tip protrusion. In another aspect said handle has an adjustable screw located near said handle's first end, said screw having a leveling pad at a first end. In another aspect said pilot drill guide is a hollow bullet-shaped pilot and said pilot is secured to said handle with an adjustable screw located near said handle's first end, said handle second end feature shape is selected from the group consisting of geometric shapes, said alpha angle may be set from 100 to 130 degrees, and said handle first end feature Beta angle may be set from 5 to 175 degrees.

In another aspect, the invention is about a method for using a three-dimensional orthopedic drill guide device comprising, providing a 3-D orthopedic drill guide comprising a handle having a first end and a second end, an extendable mechanical component having a first end and a second end, said extendable component first end connected to said handle first end, with an opening at or near said extendable component second end, said opening housing a pilot drill guide mechanically secured to said extendable component's second end, said extendable mechanical component having a lock component securing it to said handle's first end, and a device arm mechanically coupled to said handle second end at said arm near end, wherein said arm has a rotationally adjustable end feature located at said arm distal end, placing said end feature flat between the facet of the inner lateral femoral condyle and the intercondylar notch, engaging the removable hollow bullet shaped pilot bone engaging front to the lateral femoral condyle flare and the support base to the anterior cruciate ligament femoral insertion center; and drilling the femur bone towards the lateral femoral condyle flare.

Other features and advantages of the present invention will become apparent upon examining the following detailed description of an embodiment thereof, taken in conjunction with the attached drawings.

BRIEF DESCRIPTION OF THE DRAWINGS

FIGS. 1A-1B show illustrations of a proposed 3-D orthopedic femoral guide exploded assembly ((1A) Front View, (1B) Right View), according to exemplary embodiments of the invention.

FIGS. 2A-2B show illustrations of a proposed 3-D orthopedic femoral guide assembly ((2A) Front View, (2B) Right View), according to exemplary embodiments of the invention.

FIGS. 19 and 21-25 illustrate isometric views of the 3-D orthopedic guide on the femur bone (line rendering), according to exemplary embodiments of the invention.

Figure 3:
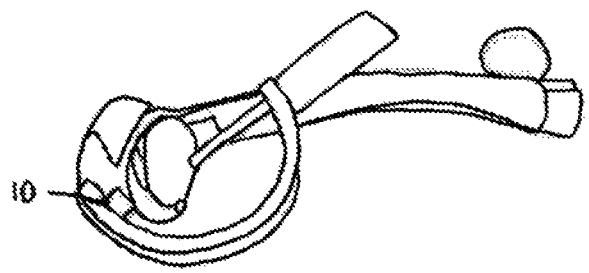
FIG. 3 illustrates an alternate shape of a 3-D orthopedic femoral guide device, according to an exemplary embodiment of the invention.
Figure 4:
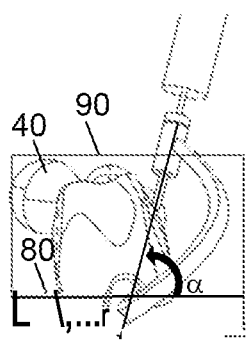
FIGS. 4-5 illustrate isometric views of the 3-D orthopedic guide on the femur bone (solid and line rendering), according to exemplary embodiments of the invention.
Figure 5:
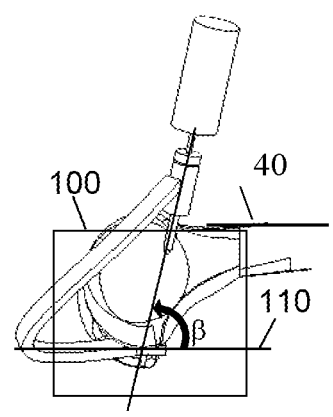
Figure 6:
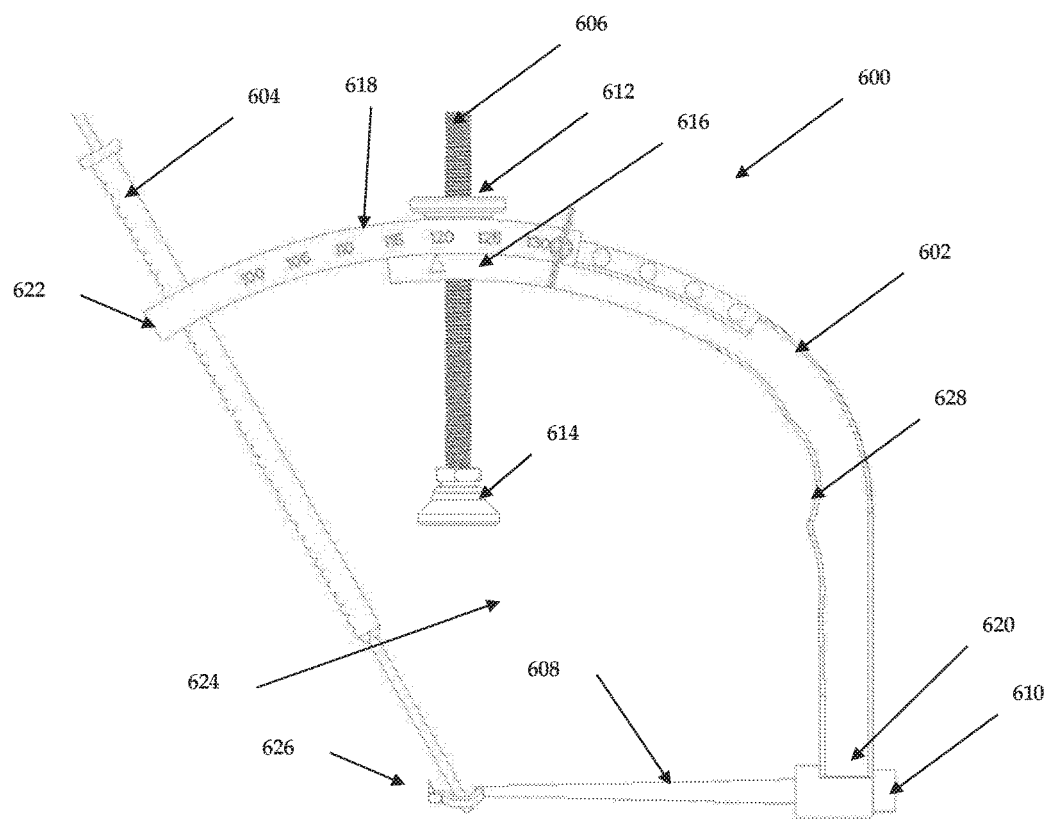
FIG. 6 illustrates a side view of a 3-D orthopedic guide including defining the Alpha angle, according to an exemplary embodiment of the invention.
Figure 7:
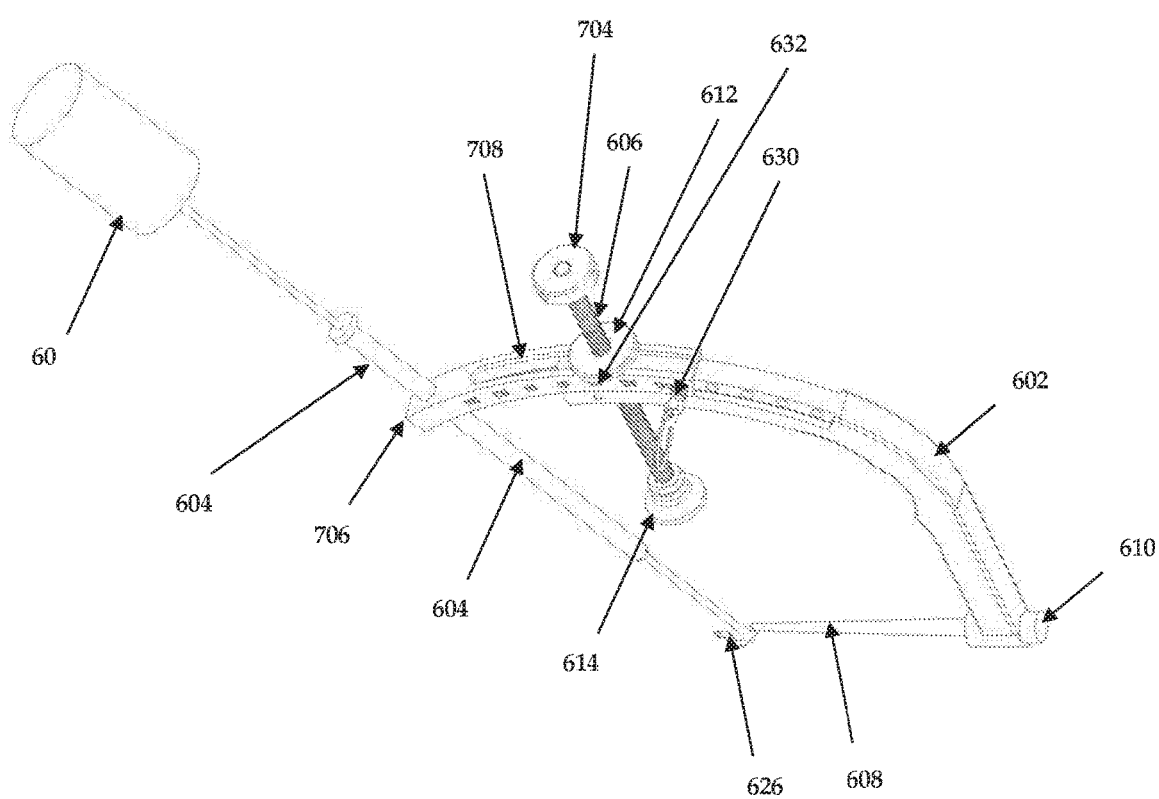
FIG. 7 illustrates an isometric view of a 3-D orthopedic guide, according to an exemplary embodiment of the invention.
Figure 8A:
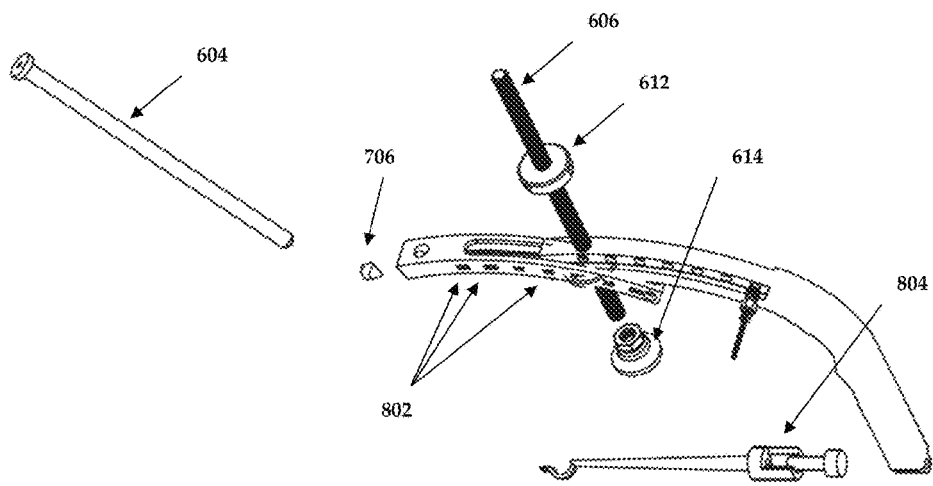
FIGS. 8A-8B illustrates the separate components of two versions of the 3-D orthopedic guide, according to exemplary embodiments of the invention.
Figure 8B:
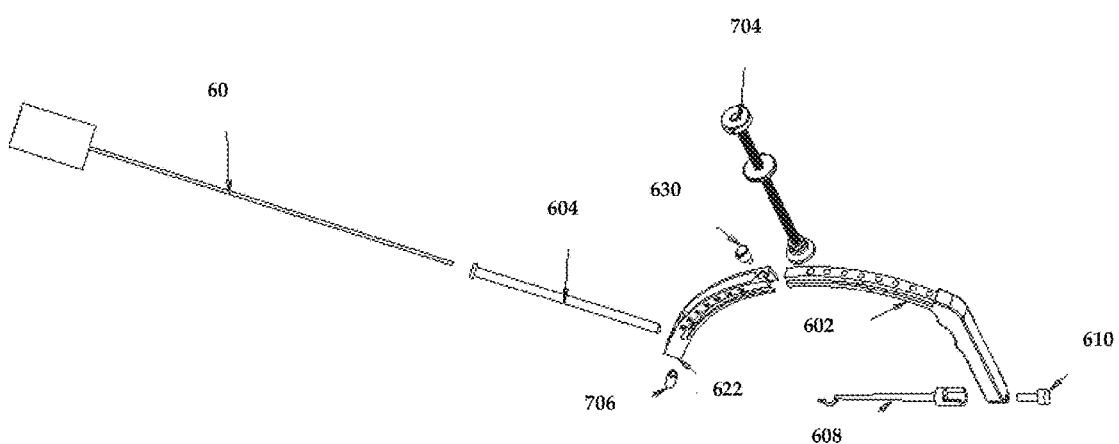
Figure 9:
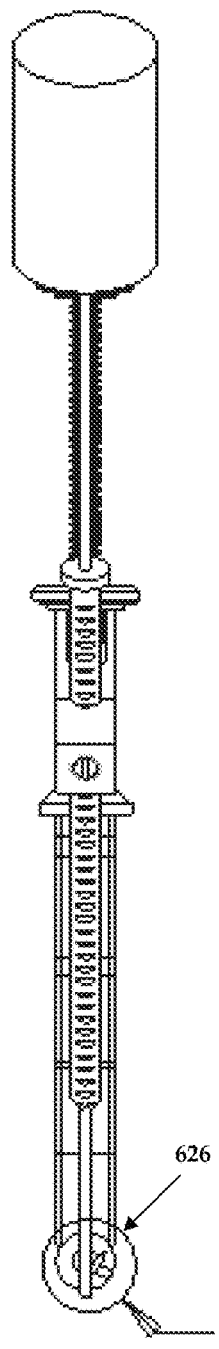
FIGS. 9-10 illustrate a front view with details of the 3-D orthopedic guide arm front including defining the Beta Angle, with details of the angle of drill, according to an exemplary embodiment of the invention.
Figure 10:
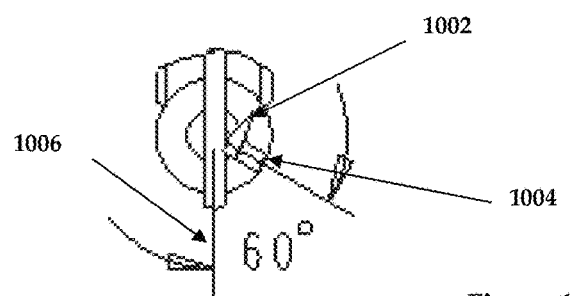
Figure 11A:
FIGS. 11A-E, and 12A-12B illustrate a side view and front view detail respectively of device arm of the 3-D orthopedic guide including various end, with details of the angle of end feature as well as the difference between left and right femur configurations, according to an exemplary embodiment of the invention.
Figure 11A:
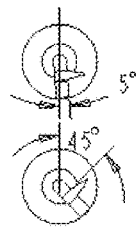
Figure 11B:
Figure 11C:
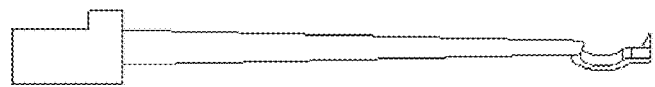
Figure 11C:
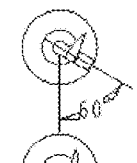
Figure 11D:
Figure 11D:
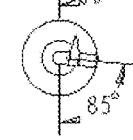
Figure 11E:
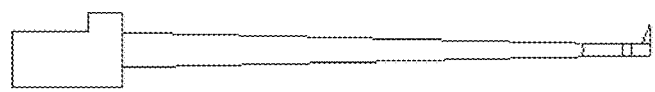
Figure 11E:
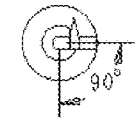
Figure 12A:
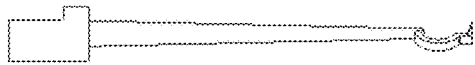
Figure 12A:
Figure 12B:
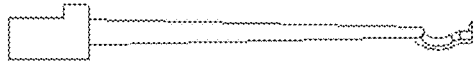
Figure 12B:
Figure 13:
FIGS. 13-14 illustrate end views of the 3-D orthopedic guide on the femur bone (solid and line rendering), according to exemplary embodiments of the invention.
Figure 14:
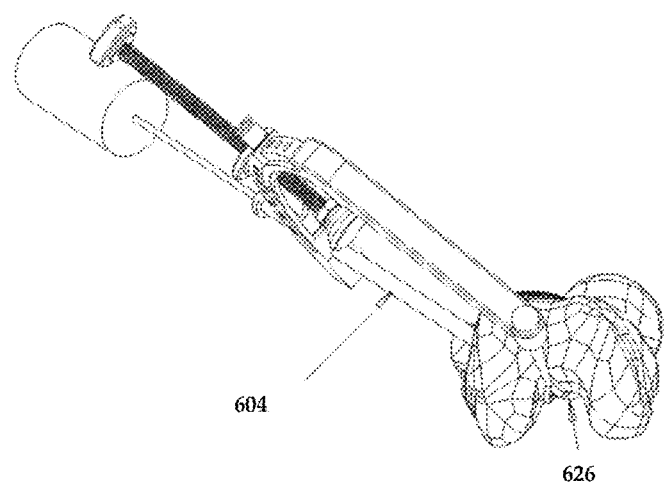
Figure 15:
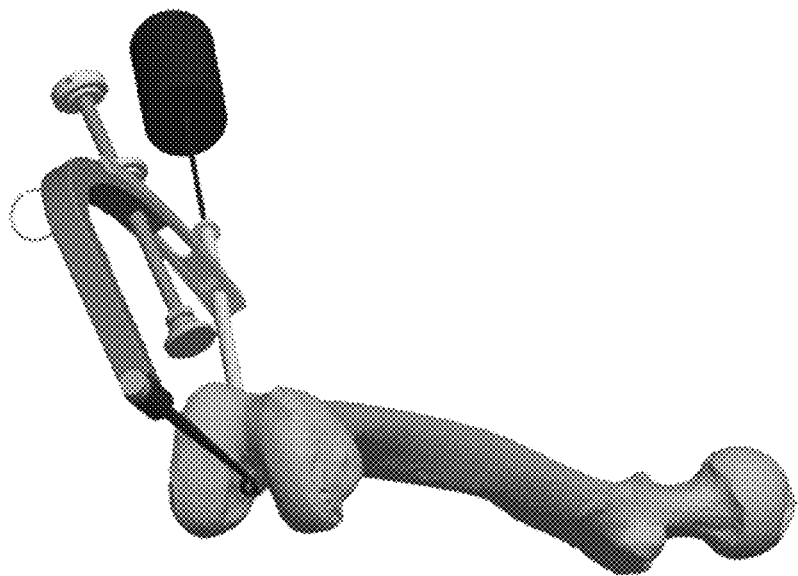
FIG. 15 illustrates an isometric view of the 3-D orthopedic guide on the femur bone (solid rendering), according to an exemplary embodiment of the invention.
Figure 16:
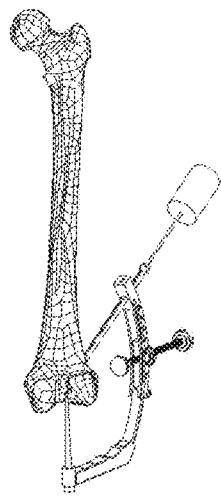
FIG. 16 illustrates an isometric views of the 3-D orthopedic guide on the femur bone (line rendering), according to an exemplary embodiment of the invention.
Figure 17:
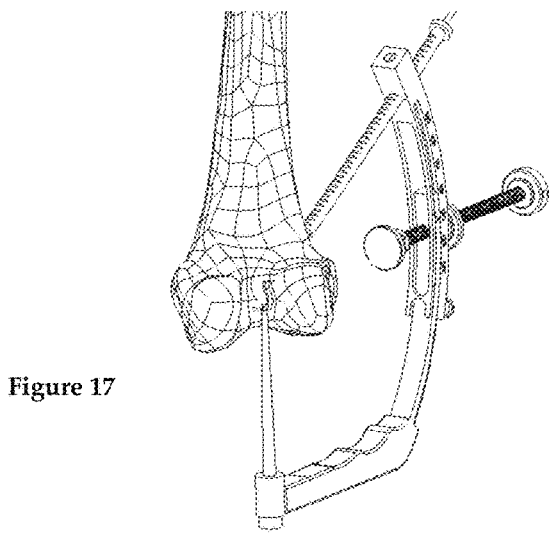
FIG. 17 illustrates an isometric views of the 3-D orthopedic guide on the femur bone (line rendering), according to an exemplary embodiment of the invention.
Figure 18:
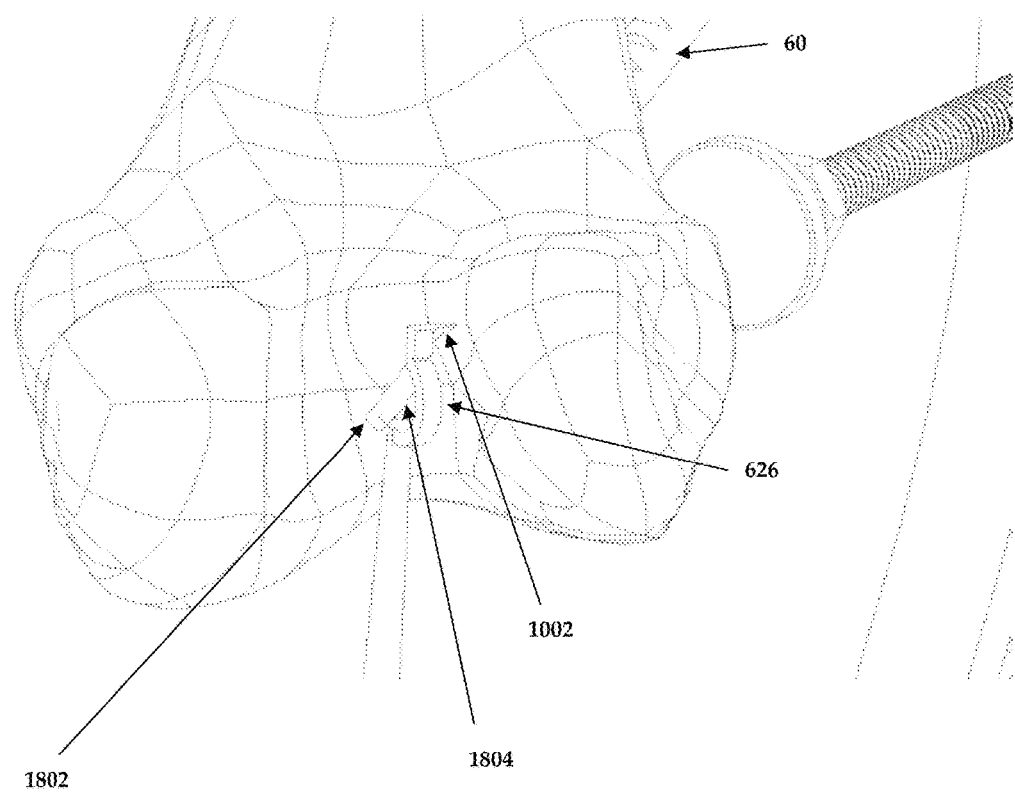
FIG. 18 illustrates an expanded view of the 3-D orthopedic guide engaging tooth on the femur bone (line rendering), according to an exemplary embodiment of the invention.
Figure 19:
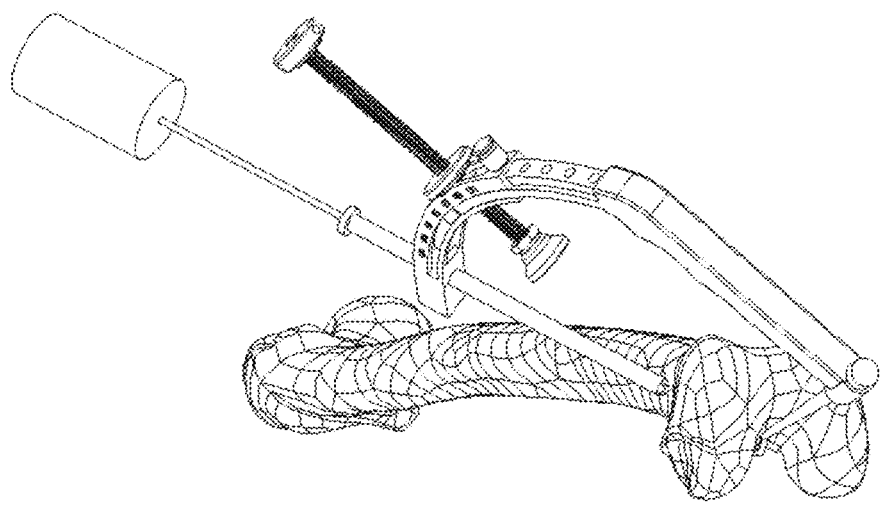
Figure 20:
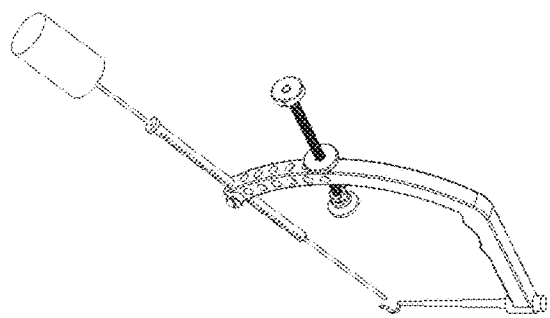
FIGS. 20 and 26 illustrate versions of a fixed angle 3-D orthopedic guide, according to exemplary embodiments of the invention.
Figure 21:
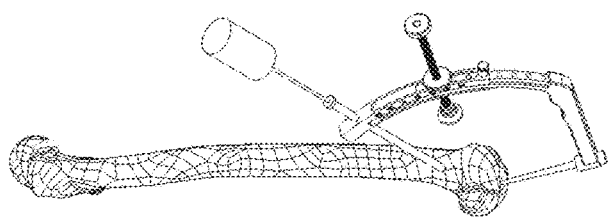
Figure 24:
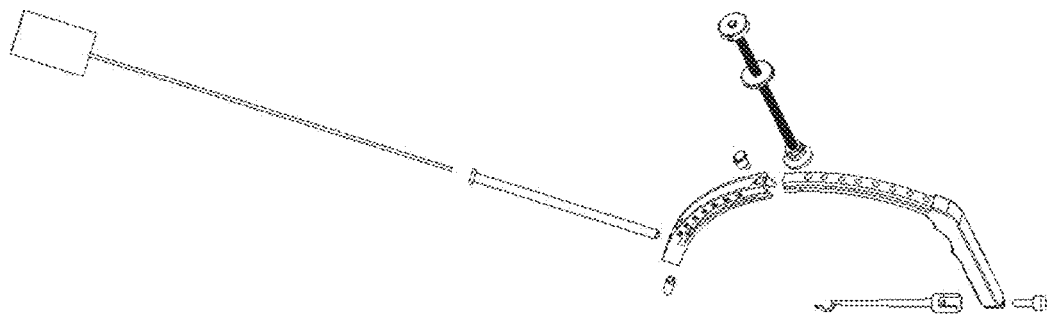
Figure 25:
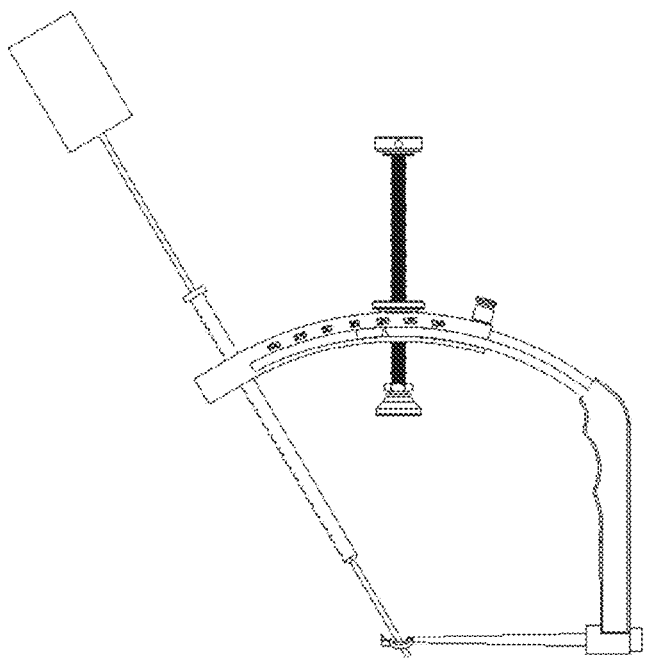

The above-described and other features will be appreciated and understood by those skilled in the art from the following detailed description, drawings, and appended claims.

DETAILED DESCRIPTION OF THE PREFERRED EMBODIMENT

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

Simplifications or omissions may be made to avoid obscuring the purpose of the section. Such simplifications or omissions are not intended to limit the scope of the present invention. All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art.

As used in the specification and claims, the singular forms "a", "an" and "the" include plural references unless the context clearly dictates otherwise. For example, the term "a transaction" may include a plurality of transaction unless the context clearly dictates otherwise. As used in the specification and claims, singular names or types referenced include variations within the family of said name unless the context clearly dictates otherwise.

Certain terminology is used in the following description for convenience only and is not limiting. The words "lower," "upper," "bottom," "top," "front," "back," "left," "right" and "sides" designate directions in the drawings to which reference is made, but are not limiting with respect to the orientation in which the modules or any assembly of them may be used.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Referring to FIGS. 1-3 we see that to drill a femoral through hole, a three-dimensional (3D) orthopedic drill guide device is used. The three-dimensional orthopedic drill guide device (FIG. 1 and FIG. 2) is comprised of an arm (10), a hollow sleeve (20), a removable hollow bullet-shaped pilot (50), and a support base (30). The arm (10) has two ends where the first end is attached to the hollow sleeve (20). The second end of the arm (10) is attached to the support base (30). The arm (10) function is to connect the hollow sleeve (20) and support base (30). The arm (10) shape avoids the contact with the patella and the thigh when the orthopedic drill guide device is installed in the femur (40). The offset distance of the arm (10) is between 20 mm or larger moving away from the knee in the inferior direction to avoid contact with the patella, and a distance between 20 mm or larger in the lateral direction to avoid contact with the thigh. The arm (30) also serves as a means for the surgeon to grasp, position, and maneuver the orthopedic drill guide device during its installation to the femur (40).

The shape combination of the arm (10), hollow sleeve (20), and support base (30) or other additional components allow the three-dimensional direction of the guide to properly direct the drill (60). For example, the arm (10) can be made of one piece that mimics the shape of an offset femoral condyle (FIG. 1 and FIG. 2), or be made of more than one piece that are combined (FIG. 3) to obtain the proper directional vector (70) for the orthopedic drill guide device.

The hollow sleeve (20) is of constant diameter for its full length, this diameter is intended to fit the outside diameter of a removable hollow bullet-shaped pilot (50). This removable hollow bullet-shaped pilot (50) will have a constant inside diameter to fit and accommodate a particular drill (60) size. The hollow bullet shape pilot (50) is used to secure the 3-D orthopedic drill guide device to the femoral bone (40) from the lateral femoral epicondylar area (42) where the drill (60) enters the femur (40). The hollow bullet shaped pilot (50) may incorporate a knurled knob (52) at one end to facilitate insertion and removal into the hollow sleeve (20).

The removable hollow bullet shaped pilot (50) has a least one bone engaging tooth (54) at the other end to keep orthopedic drill guide in place when assembled. The hollow bullet-shape pilot (50) inside diameter accurately accommodates a particular drill (60) size and it can be inserted and removed from the hollow sleeve (20) to allow changing the hollow bullet shape pilot (50) of different inside diameters. The hollow bullet shape pilot (50) may be retained within the hollow sleeve (20) during use of a threads or any other suitable means that prevents the hollow bullet-shape pilot (50) to turn with the drill (60) during drilling.

The support base (30) is attached to the second end of the arm (10). The support base (3) is positioned by the surgeon to the original anatomical ACL's femoral insertion center (44). The hollow bullet shape pilot (50) is then pressed and locked to the femur (40) allowing assembly of the orthopedic guide device. Once the orthopedic guide device is locked into position the surgeon proceeds to drill (60) the femur (40) entering from the lateral femoral condyle flare (42) and emerging at the origin of the ACL (44) on the posteromedial aspect of the lateral femoral condyle where the support base (30) is located.

The orientation of the drill is predetermined by the 3-D orthopedic drill guide. The directional vector (70) of the 3-D orthopedic drill guide is achieved by rotating degrees measured from the coronal plane (80) when facing the axial plane (90), and rotating degrees about the coronal plane (110) when facing the sagittal plane (100). The 3-D orthopedic drill guide needs a set of right and left instruments to obtain the appropriate Alpha and Beta angles, variously provided by either adjustable or fixed mechanical components and/or handles/end arms. The 3-D orthopedic drill guide can be machined and/or formed from non-corrosive metals.

Novel features of the 3-D orthopedic drill guide device include the following; (A) The guide provides the correct directional vector for the drill that avoids damage to soft tissue. The surgeon does not have to maneuver the drill guide to obtain the correct drill direction. (B) Surgery is completely performed at a 90 degree flexion. This avoids repositioning the patient to perform the surgery. Repositioning the patient may interrupt surgeons' vision to drill the bone tunnel. (C) The installed tissue repair device is completely inside the tunnel with a safe, predictable, and reproducible tunnel length of more than 20 mm. A tunnel length larger than 20 mm minimizes stress concentration and promotes biological integration of the tissue repair device. This minimizes rupture of the tissue repair device during its use. (D) Bone-Tendon-Bone tunnel mismatch can be accommodated optimizing fixation. (E) Direction of tunnel reduces tension applied to the graft. (F) Predictable tunnel length. (H) Safe and reproducible tunnel placement. (I) Biological integration is favored through a longer tunnel (J) It avoids contact between the orthopedic drill guide device with the patella bone and/or the thigh. (K) 3-D orthopedic drill guide arm can be used to grasp guide into position when drilling. This allows for better support and direction of the drill.

While this drill guide device is intended primarily for use in the implantation of ACL tissue repair device, its convenience to drill bone enable it to be used in other applications.

Referring to FIGS. 6-15 we see another embodiment of the 3-D orthopedic drill guide 600 invention. It is comprised of an arcuate main body (for easier human hand handling as well as bone clearance), forming a handle 602 with optional finger indentation(s) 628. Said handle 602 connects the arm to an adjustable extendable slider 618 along said handle's 602 first end 616, and a thumb screw 610 located at said handle's 602 second end 620 from which a device arm 608 extends. To ease use, the slider has calibrated angular indications 802 and a reference point 632. A release plunger 630 or similar device is used to set the length of extension of said extendable slider 618, which in turn adjusts the angle of the drill 60, which we will term the Alpha angle.

A screw 606 is located near the first end 616, with a thread on said handle 602 so that rotation of said screw 606 causes its extension/retraction from the inner arc area 624. The extendable slider 618 slides in/out of the handle 602 first end 616, and has an opening at the distal end that houses a fixed or removable pilot drill guide, such as a hollow bullet-shaped pilot 604 or similar, which is secured through mechanical component locks. In one embodiment, this is a lock screw 706 attached at said extendable slider 618 distal end 622, wherein said lock screw 706 used to hold in place the bullet shaped pilot or bullet 604 which is used to guide the drill 60 as well as to get purchase with the distal lateral femur.

The thumb screw 610 attaches the device arm 608 to the handle's 602 second end 620 and serves to secure the device arm 608. It must be pointed out that the invention is prepared as a right side and left side device (for the respective right and left human knees), resulting in mirror images of the front view shown in FIGS. 9-10, primarily defined by the 'tip' 1002 'up' side. In that respect, the discussed Alpha angle (the angle of the drill bullet 604 respective to the vertical (similar in direction to that of the screw axis 606 as seen from the side) as shown FIG. 6. Said Alpha angle may range from 90 to 180 degrees, but the favorites angles for femur surgery are 100 to 130. This alpha angle, is combined with the end feature 626 or Beta Angle 1004 (the angle 1004 of the end feature 626 as measured from the bottom projection of the axis 1006 of the drill 60 projection as seen from the front. Once the end feature 626 is placed against the fascia of the bone, the angle formed by the combination of the Alpha and Beta angles, forms the Gamma angle on which the ACL tunnel is bored on the bone. The above Gamma angle is a critical guidance to the surgeon, in generating a resultant ACL tendon tension vector (the resultant Alpha/Beta dependent drill orientation of the tunnel).

In one embodiment, the end feature beta angle 1004 (Beta Angle) of this attachment has been found to be optimal at or about 60 degrees (FIG. 10), although variations from 5 to 175 degrees (on either side of the drill axis 1006, depending on whether the tool is configured for a right or left femur surgery (FIG. 12). Of course, the angle may be brought as low as 0 deg. or as high as 180 deg. (with the risk of the drill impacting the end feature 626 when it comes out of the femur), but in practice the tip 1002 up requirement limits it to 5 to 120 degrees. However, past 90, the drill would be opposite the desired place of entry on the femur. The end feature 626 shape and angle 1004 are driven so that the drill bit 1802 exit avoids contact with any arm portions.

In one embodiment, this angle adjustment is built into the device arm base 804, so that when the device arm 608 is attached to the handle 602 via said thumb screw 610, the end feature 626 angle (Beta angle) is optimally set at 60 degrees off the drill datum (the plane 1006 on which the drill 60 sits). This angle offset adjusts the angle at which said end feature 626 contacts the fascia of the bone. In another embodiment, the angle 1004 of said end feature 626 is made to be infinitely adjustable (so that when the desired angle is met), the thumb screw 610 is tightened.

The angle of the end feature 626 is critical, for this will contact the femur interchondilar notch, and defines the Beta angle of the drill. In one embodiment, the device arm 608 has an homogeneous width. In an alternate embodiment, the end feature is primarily comprised of an area that is significantly wider than the end arm's cross section (this area may be round, square, flat, semi-round, C-shaped, and/or any suitable shape), so that said end feature surface when lying against the fascia of the bone (i.e. femur or similar bone) defines both the Beta angle 1004 of the 3D tool 600 and provides sufficient purchase to ensure the drill hole and subsequent ligament lies at an optimal angle to said bone fascia). The adjustment of this end feature angle 1004 to the bone fascia, provides the critical drill angle.

In one embodiment, said end feature 626 has a bone engaging feature 1002 (such as a tooth, beak, tip or other suitable feature to facilitate securing said end feature 626 to the bone). This beak has a number of uses. As mentioned above, it provides a degree of mechanical attachment to the bone fascia. In addition, it provides a sense of drill exit opening 1804 on the bone navigation to the surgeon, as the drill bit tip 1802 will exit a specific distance from said beak. In one embodiment, said distance is preferred to be about 6 mm, although any suitable distance may be selected. Similarly, the shape of the end feature 626 is preferred to be one that allows free operation of the drill bit tip 1802.

The screw 606 has an inside leveling pad 614 at the inside en end, which assists the guide to remain in place and contact the outer skin. This helps the surgeon place the tool and keeps it in place in case the surgeon has to use the tool-holding hand temporarily somewhere else. The outside leveling screw 704, and a thumb screw slider 612 which locks the slider to the handle. The leveling screw 704 assists the guide to remain in place and may contact the outer skin. At or near the first end 616 of the handle, there is an easy to adjust mechanical lock component 630 that controls the extension of the slider 618 inside the handle 602. In one embodiment, said mechanical lock component is a releasable plunger 630 whose removal releases the slider to move inside the handle 602, and operates in connection with a thumb screw slider which locks the slider to handle, with the adjustment resulting in which of the openings 802 the plunger goes, effectively adjusting the overall length of the handle/slider (602/618) through the slider 708, which has an indicated degree to define the drill vector. In another embodiment, the end feature 626 is separately rotatably adjustable from said device. Note that the end arm may be at 0 degrees Beta, with the actual end feature 626 being the bent component to the desired Beta angle (5 to 175 to the left of the datum 1006) or (5 to 175 to the right of the datum 1006).

In an alternate embodiment, the adjustable component for the Beta angle is comprised of one or more mechanical plugs, designed to be mechanically attached to the first end of the handle (and or to each other, forming a plug chain), so that the angle may adjusted, but in a semi-fixed form. Say one 10 deg. plug, or three 15 degree plugs. The distal link on said chain (where the near end is attached to the handle first end) has the pilot drill guide components as described above.

Figure 26:
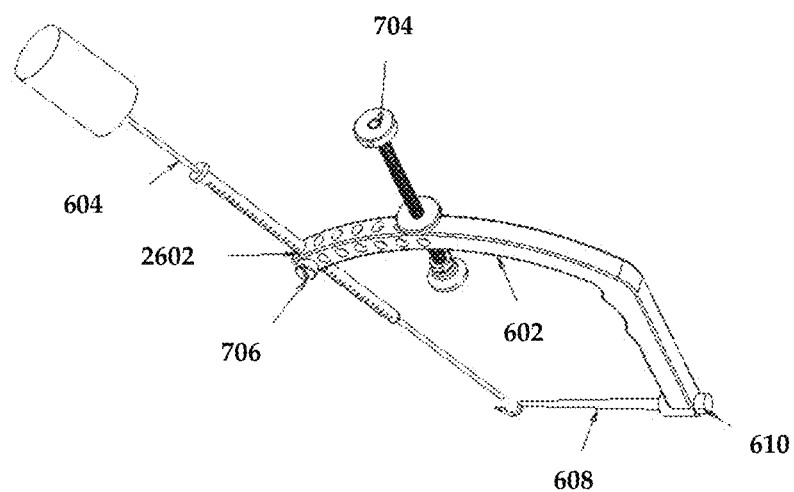

In an alternate embodiment (FIG. 26), the adjustable components of the unit are obviated partially or fully. The first such component is the extendable slider 618, which is replaced by the first length of the handle 602, which extends to a fixed drill angle for the device (with minimal adjustments). As before, the first end of said handle 602 has one or more other openings 2602 which house at/near the distal end a drill bit bullet lock mechanical components (e.g. lock screw 706 or similar) attached at said the selected opening 2602 which holds in place the bullet shaped pilot or bullet 604 which is used to guide the drill 60 as well as purchase with the distal lateral femur. The fixed angle may be any, although about 120 degrees has been found to be optimal. Thus one or more units (e.g. 100, 110, 115, 120, 125, 130, 140) may be part of a surgical kit.

The second adjustable component that may be obviated is the device arm 608, and the end feature angle 1004. Combinations of the above may be featured. One such embodiment is simple, fixed Alpha and Beta angle device, that resembles a C, where one end holds the bullet 604 at a fixed Alpha angle (selected from a range of 90 to 150 degrees), and the end feature is angled at a fixed beta angle selected from (5 to 175 degrees) on either side of the datum (drill bill front view).

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the foregoing description of embodiments.

The invention claimed is:

1. A method for using a three-dimensional orthopedic drill guide device comprising:
   providing a three-dimensional orthopedic drill guide device comprising: a handle having a first end and a second end; an extendable mechanical component having a first end and a second end, said extendable component first end connected to said handle first end, with an opening at or near said extendable component second end, said opening housing a pilot drill guide mechanically secured to said extendable component's second end, said extendable mechanical component having a lock component securing it to said handle's first end; and a device arm mechanically coupled to said handle second end at said arm near end, wherein said arm has a rotationally adjustable end feature located at said arm distal end, wherein said device arm end feature covers an area which is wider than that of said device arm, with said device arm end feature having an opening to allow a drill bit to pass through, wherein; said device arm end feature has a tip protrusion, wherein said handle has an adjustable screw located near said handle's first end, said screw having a leveling pad at a first end
   placing said end feature flat between the facet of the inner lateral femoral condyle and the intercondylar notch;
   engaging the pilot bone engaging front to the lateral femoral condyle flare and the support base to the anterior cruciate ligament femoral insertion center; and
   drilling the femur bone towards the lateral femoral condyle flare.

2. The method of claim 1 wherein;
   said device arm end feature covers an area which is wider than that of said device arm, with said device arm end feature having an opening to allow a drill bit to pass through.

3. The method of claim 2 wherein;
   said device arm end feature has a tip protrusion.

4. The method of claim 3 wherein;
   said handle has an adjustable screw located near said handle's first end, said screw having a leveling pad at a first end.

5. The method of claim 4 wherein;
   said extendable mechanical component is a slider and said slider lock component is a releasable plunger;
   said slider distal end opening houses a hollow bullet-shaped pilot, and said pilot is secured to said slider with an adjustable screw located near said slider's distal end;
   said device arm end feature shape is selected from the group consisting of geometric shapes;
   said device arm mechanical coupling to said handle is a thumb screw;
   said alpha angle may be set from 100 to 130 degrees; and
   said beta angle may be set from five to 175 degrees.

6. The method of claim 5 wherein;
   said extendable mechanical component is comprised of a plug chain of one or more mechanical plugs and said lock component is comprised of a mechanical component;

the final plug forming said plug chain distal end houses a hollow bullet-shaped pilot, and said pilot is secured to said plug chain distal end with an adjustable screw;

said device arm end feature shape is selected from the group consisting of geometric shapes;

said device arm mechanical coupling to said handle is a thumb screw;

said alpha angle may be set from 100 to 130 degrees; and said alpha angle may be set from five to 175 degrees.

\* \* \* \* \*